United States Patent [19]

Moon et al.

[11] Patent Number: 5,656,466
[45] Date of Patent: Aug. 12, 1997

[54] PROCESS FOR PREPARING VIRUS-RESISTANT TRANSGENIC PLANT

[75] Inventors: Young-Ho Moon, Kuri; Kyu-Whan Choi, Seoul; Hong-Seob Jeon, Seoul; Chul-Hwan Kim, Seoul; Man-Keun Kim, Seoul, all of Rep. of Korea

[73] Assignee: Jinro Limited, Seoul, Rep. of Korea

[21] Appl. No.: 319,622

[22] Filed: Oct. 6, 1994

[30] Foreign Application Priority Data

Jul. 21, 1994 [KR] Rep. of Korea .................. 94 17696

[51] Int. Cl.$^6$ .............. A01H 1/04; C12N 15/00; C12N 5/14
[52] U.S. Cl. ............... 435/172.3; 435/69.1; 435/320.1; 435/252.3; 800/205; 800/DIG. 42; 536/23.6
[58] Field of Search ................. 435/172.3, 69.1, 435/240.49, 252.3, 320.1, 240.4; 536/23.6; 935/9; 800/205, DIG. 42

[56] References Cited

PUBLICATIONS

Owens, R. A. et al., A Possible Mechanism for the Inhibition of Plant Viruses by a Peptide from Phytolaca americana, Virology, 56:390–393(1973).

Irvin, J. D. et al., Pruification and Partial Charaterization of the Antiviral Protein from Phytolacca americana Which Inhibits Eukaryotic Protein Synthesis, Arch. Biochem. Biophys., 169:522–528(1975).

Irvin, J. D. et al., Purification and Properties of a Second Antiviral Protein from Phytolacca americana Which Inactivates Eukaryotic Ribosomes, Arch. Boichem. Biophys., 200:418–425 (1980).

Lin, Q. et al., Isolation and Characterization of a cDNA Clone Encoding the Antiviral Protein from Phytolacca americana, Plant Mol. Biol., 17:609–614(1991).

Ready, M. P. et al., Extracellular Localization of Pokeweed Antiviral Protein, Proc. Natl. Acad., USA, 83:5053–5056(1986).

Nejidat, A. et al., Engineered Resistance against Plant Virus Diseases, Physiol. Plant., 80:662–668(1990).

Cuozzo M. et al., Viral Protection in Transgenic Tobacco Plants Expressing the Cucumber Mosaic Virus Coat Protein or Its Antisense RNA, bio/Technology, 6:549–557(1988).

Lodge et al (Aug. 1993) Proc. Natl Acad. Sci USA 90:7089–7093.

*Primary Examiner*—David T. Fox
*Assistant Examiner*—Elizabeth F. McElwain
*Attorney, Agent, or Firm*—Darby & Darby, P.C.

[57] ABSTRACT

The present invention provides a process for preparing a transgenic plant producing antiviral protein, which is transformed with a recombinant vector for *Phytolacca insularis* antiviral protein(PIP) expression. In accordance with the present invention, a recombinant expression vector for *Phytolacca insularis* antiviral protein made a grant of broad vital-resistance to transgenic plant transformed therewith, grounded on the expression of PIP.

4 Claims, 6 Drawing Sheets

FIG. 1

```
ATGAAGTTGATGCTTGTGGTGACAATATCAGTATGGCTCATTCTTGCACCAACATCTACT
 M  K  L  M  L  V  V  T  I  S  V  W  L  I  L  A  P  T  S  T

TGGGCCGTGAATACCATCATCTACCATGTTGGAAGTACCACCATTAGAAACTATGCAACT
 W  A  V  N  T  I  I  Y  H  V  G  S  T  T  I  R  N  Y  A  T

TTTGGATACTTCGTACTGAAGGCGAAGATCCAAGTTATGTGCTATGGAATACCAATGCTG
 F  G  Y  F  V  L  K  A  K  I  Q  V  M  C  Y  G  I  P  M  L

CCCAATATTGGATCAAATCCAAAATACATATTGGTTGAGCTCCAAGGTTCAAATGAAGAA
 P  N  I  G  S  N  P  K  Y  I  L  V  E  L  Q  G  S  N  E  E

GGCATCACACTAATGCTAAGACGAAACAATTTATATGTGATGGGCTATTCTGATCCCTAC
 G  I  T  L  M  L  R  R  N  N  L  Y  V  M  G  Y  S  D  P  Y

AACAATAGGTGTCGTTTCCATCTCTTTAAGGCTATCTCAGGTACTGAACGCGAAGATGTA
 N  N  R  C  R  F  H  L  F  K  A  I  S  G  T  E  R  E  D  V

GAGACTACTCTTTGCCCAAATGCCGATTCTCGTGTTGGTAAAAACATAAACTATGATAGT
 E  T  T  L  C  P  N  A  D  S  R  V  G  K  N  I  N  Y  D  S

CGATATCCAACATTGGAATCAAAAGCAGGAGTAAATTCAAGAAGTCGAGTCCAACTGGGA
 R  Y  P  T  L  E  S  K  A  G  V  N  S  R  S  R  V  Q  L  G

ATTCGAATACTCGACAGTGGCATTGGAAGGATTTCTGGAGTGACGTCATTCACTGAGAGA
 I  R  I  L  D  S  G  I  G  R  I  S  G  V  T  S  F  T  E  R

ACCGAAGCTGAATTCCTACTGGTAGCCATACAAATGGTATCAGAGGCAGCAAGATTCAAG
 T  E  A  E  F  L  L  V  A  I  Q  M  V  S  E  A  A  R  F  K

TACATAGAGGATCAAGTGAAAACTAATTTTAACAGACCATTCAACCCTAATCCCAAAGTA
 Y  I  E  D  Q  V  K  T  N  F  N  R  P  F  N  P  N  P  K  V

CTTATATTGCAGGAGACATGGGGTAAGATTTCTTCAGCAATTCATGGTGCCAGGAATGGA
 L  I  L  Q  E  T  W  G  K  I  S  S  A  I  H  G  A  R  N  G

GTTTTACCCAATCCTCTACAGCTAGTGCATGCCAATGGTGCAAATTGGATAGTGTTGAGA
 V  L  P  N  P  L  Q  L  V  H  A  N  G  A  N  W  I  V  L  R

GTGGATGAAATCAAGCCTGATGTGTCACTCTTAAACTACGTTATTGGGAGCTGCCAGAGA
 V  D  E  I  K  P  D  V  S  L  L  N  Y  V  I  G  S  C  Q  R

ACTTATAACCAAAATGCCATGTTTTCTCAACTTATAATGTCTACTTATTATAATTACATG
 T  Y  N  Q  N  A  M  F  S  Q  L  I  M  S  T  Y  Y  N  Y  M

GCTAATCTTGGTGATTAG
 A  N  L  G  D  *
```

PROCESS FOR PREPARING VIRUS-RESISTANT TRANSGENIC PLANT

FIELD OF THE INVENTION

The present invention relates to a process for preparing a transgenic plant, more specifically, a process for preparing a virus-resistant transgenic plant transformed with a recombinant expression vector for antiviral protein from *Phytolacca insularis Nakai*.

BACKGROUND OF THE INVENTION

Since plants can not escape from applied pathogens because of their immobile nature, they must be able to defend themselves by direct or indirect response to the pathogenic challenge; and, most plants appear to undertake some general defense mechanism to protect themselves against infective pathogens, e.g., fungi, bacteria and virus.

In this connection, crude extract isolated from *Phytolacca americana L.* has been proved to inhibit in vivo synthesis of polypeptide(see: Owens, R. A. et al., Virology, 56:390–393 (1973)); and, said report has accelerated studies on the Phytolacca antiviral protein(hereinafter referred to as "PAP") isolated from *Phytolacca americana L.* Under the circumstances, PAPs such as PAP-I and PAP-II produced in spring and summer, respectively, and PAP-S produced from seed, have been discovered and isolated since the early 1970's(see: Irvin, J. D. et al., Arch. Biochem. Biophys., 169:522–528(1975); Irvin, J. D. et al., Arch. Biochem. Biophys., 200:418–425(1980)).

As a result of extensive studies on the PAP at the molecular level, it was determined that PAPs block the 60S ribosomal subunit of eucaryotic polypeptide synthesis machinery, which is a general phenomenon in light of the fact that other ribosome-inactivating proteins(RIPs) inactivate said subunit; and, structure and base sequence of PAP genome, a multigene family, have been elucidated(see: Lin, Q. et al., Plant Mol. Biol., 17:609–614(1991)). Further, it has been also reported that: PAP is synthesized and secreted from the cytosol and it is involved in the control of pathogenic virus; however, the detailed mechanism of virus inactivation has not been proved(see: Ready, M. P. et al., Proc. Natl. Acad. Sci., USA, 83:5053–5056(1986)).

On the other hand, many methods have been developed in attempts to prepare transgenic plants to confer resistance against viruses. These include methods of expression of genes encoding viral coat proteins(see: Nejidat, A. et al., Physiol. Plant., 80:662–668(1990)) and cucumber mosaic virus coat protein in tobacco plants(see: Cuozzo M. et al., Bio/Technology, 6:549–557(1988)). However, none of these attempts have revealed to be practicable in light of the level of protection against viruses and the spectrum of target viruses.

Accordingly, there is a need in the art for the development of a practicable transgenic plant to guarantee stable expression of variable antiviral proteins originated from eucaryotes as well as procaryotes and to confer broad viral resistance spectrum against diverse pathogenic viruses.

Under the circumstances, the present inventors designed a recombinant expression vector, which contains PIP gene isolated from cDNA library of *Phytolacca insularis Nakai* autogenous in Korea(see: U.S. Pat. No. 5,348,865); and, developed a transgenic potato plant transformed with the recombinant vector for *Phytolacca insularis* antiviral protein(hereinafter referred to as "PIP") comprising the PIP gene.

SUMMARY OF THE INVENTION

In accordance with the present invention, it has been discovered that: PIP is manufactured in a transgenic plant transformed with a recombinant PIP expression vector and said transgenic plant has broad-spectrum of viral resistance against diverse pathogenic viruses.

A primary object of the present invention is, therefore, to provide a novel recombinant vector containing the PIP gene isolated from a cDNA library of the *Phytolacca insularis Nakai*.

Other objects of the present invention are to provide a process for preparing a virus-resistant transgenic plant transformed with said recombinant vector, and to provide a method of conferring viral resistance against pathogenic viruses upon plants.

BRIEF DESCRIPTION OF DRAWINGS

The above and the other objects and features of the present invention will become apparent from the following description given in conjunction with the accompanying drawings, in which:

FIG. 1 is the full nucleotide sequence SEQ. I.D. NO. 1 of the PIP gene and amino acid sequence SEQ. I.D. NO. 2 translated therefrom(SEQ ID NO: 1 and SEQ ID NO: 2);

DETAILED DESCRIPTION OF THE INVENTION

Figure 2:
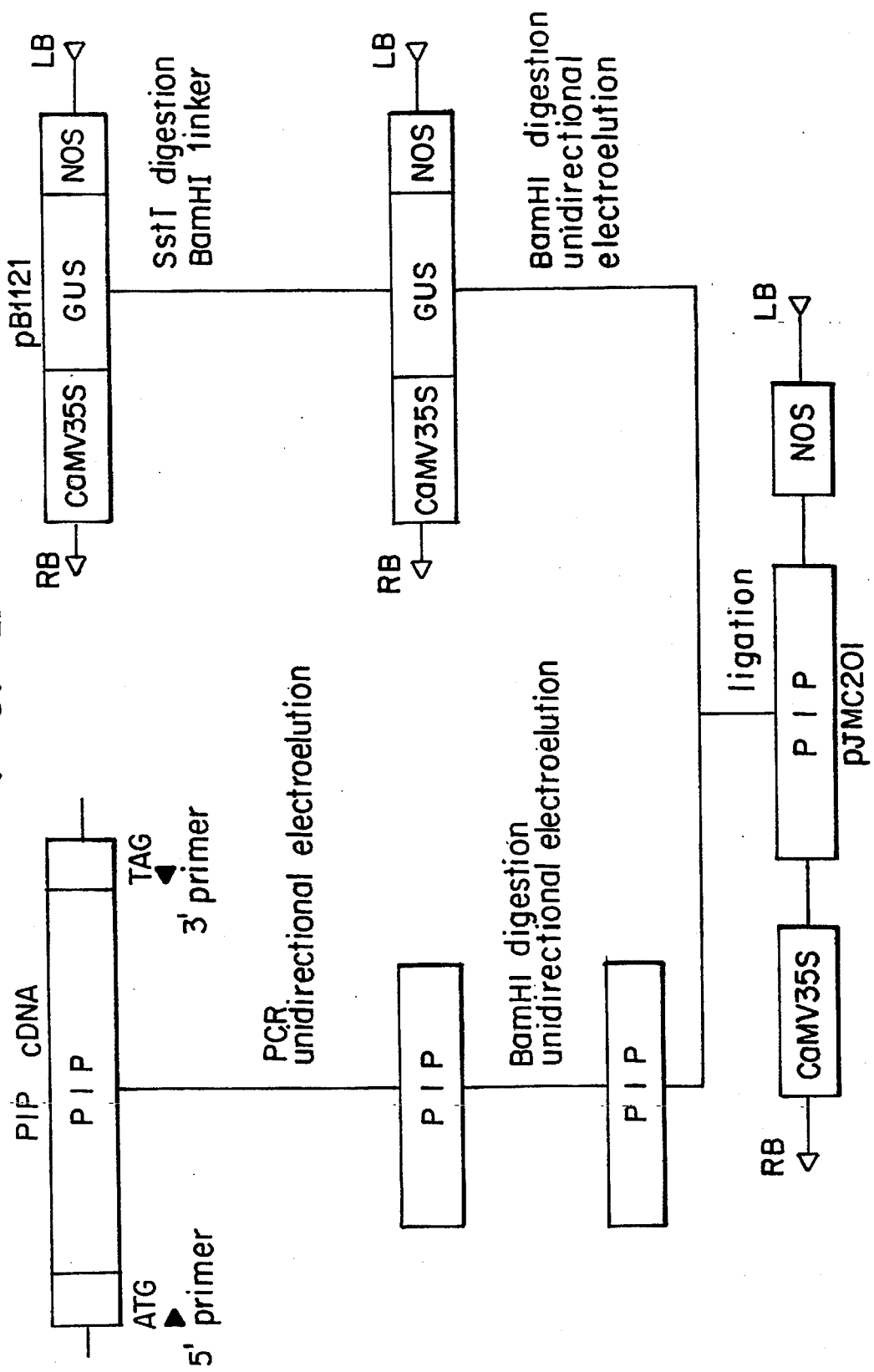
FIG. 2 is a stepwise construction scheme of expression vector pJMC201.

The present inventors first developed a recombinant expression vector pJMC201 containing PIP gene isolated from a cDNA library of *Phytolacca insularis Nakai* and produced a transgenic plant transformed therewith by the aid of a mediator, i.e., *Agrobacterium tumefaciens*.

To isolate PIP gene, the inventors purified total cellular mRNA from leaves of *Phytolacca insularis Nakai* obtained in Korea and constructed a cDNA library therefrom. PIP gene was isolated from cDNA library by employing PAP gene which is phylogenically related to the PIP gene. DNA sequence of PIP gene was determined in accordance with Sanger's dideoxy chain termination method.

For the expression of isolated PIP gene, the PIP cDNA was amplified by polymerase chain reaction(hereinafter referred to as "PCR"). The amplified cDNAs were isolated by unidirectioanl electroelution, and then digested with BamHI restriction enzyme. pJMC201, the recombinant vector for the expression of PIP, was constructed by ligating BamHI fragment with a binary vector pBI121(Clonetech, Lot #6019-2, USA). *Agrobacterium tumefaciens* LBA 4404, a well-known mediator for plant cell transformation, was transformed with said pJMC201 and transgenic plant cell was prepared by transforming with said organism. Shoots were induced from the transgenic plant cell on MS selective medium containing 500 mg/l carbenicillin and 100 mg/l kanamycin; and root was generated from said shoots. The plant thus obtained was transferred to pot for continuous growth.

Proper insertion of PIP gene to the genome of transgenic potato was identified by Southern blot analysis and its transcription was also verified. Resistance of transgenic plant for diverse viral infection was tested by ELISA method. The results demonstrated that: transgenic potato plant was properly transformed with the recombinant vector; PIP was expressed from the transgenic plant in a successful manner; and, virus proliferation was efficiently inhibited by the expressed recombinant PIP in the transgenic potato.

In accordance with the present invention, a recombinant expression vector for PIP made a grant of viral resistance to transgenic plant transformed therewith, grounded on the production of PIP; and, therefore, it was suggested that the recombinant PIP produced therefrom can be applied for the development of antiviral agents in a practical manner.

The present invention is further illustrated by the following examples, which should not be taken to limit the scope of the invention.

EXAMPLE 1

Isolation of PIP Gene

Leaves of *Phytolacca insularis Nakai* originated in Ulung-Do in Korea were homogenated and centrifugation was carried out to obtain supernatant. To eliminate proteins and impurities from the supernatant, phenol/chloroform extraction and chloroform extraction were carried out in a serial manner; and, mRNA was isolated from total cellular RNA using oligo(dT) cellulose column chromatography. The mRNA thus isolated was used for cDNA synthesis employing ZAP-cDNA synthesis Kit (Stratagene, UK). Fractionation of synthesized cDNA was carried out and cDNAs thus fractionated were ligated with Uni-Zap XR vector(Stratagene, U.K.), and in vitro packaging employing packaging extract followed.

To isolate PIP gene from the cDNA library prepared, PAP gene which is genetically related to PIP gene, was isolated from cDNA library of *Phytolacca americana L.* and, about 0.5 kb EcoRI fragment of said PAP gene was labelled with DIG-Labelling & Detection Kit(Boehringer Mannheim, Germany); and, resultant thus labelled was employed as a probe for PIP gene isolation. Then, *E. coli* XL1-Blue was infected with the above packaged phage to screen recombinant Uni-Zap XR phages. To transfer phagemids of recombinant Uni-Zap XR phages obtained by screening, in vivo excision technique employing R408 helper phage was carried out. Plasmids were isolated by alkali lysis method from the colonies thus selected, and colonies harboring PIP gene were screened by hybridization with the labelled EcoRI fragment of PAP gene(about 0.5 kb).

Clones showing large spot in the course of hybridization were selected and subcloned on pBlueScript SK(−) vector. Nucleotide sequence of PIP gene was determined in accordance with Sanger's dideoxy chain termination method(see: Sanger, F., Science, 214:1205–1210(1981)). FIG. 1 is the full nucleotide sequence of the PIP gene and amino acid sequence translated therefrom(SEQ ID NO: 1 and SEQ ID NO: 2). As can be seen in FIG. 1, PIP cDNA consists of an open reading frame of 918 base pairs including translation initiation and termination codons.

EXAMPLE 2

Preparation of Expression Vector pJMC201

To express the PIP gene prepared in Example 1 by employing CaMV 35S promoter, PIP cDNA was amplified by PCR employing 5'-CGGGATCCAGCTAGTAGGAAGGGAAGATG-3' (SEQ ID NO: 3) as the N-terminal primer and 5'-CGGGATCCAAACTAATCACCAAGATTAGC-3'(SEQ ID NO: 4) as the C-terminal primer. Each cycle of PCR needed denaturation(95° C., 30 sec), annealing(55° C., 30 sec) and extension (72° C., 30 sec), and to effective amplification were 30 cycles required. The amplified cDNAs were isolated by unidirectioanl electroelution, and then digested with BamHI restriction enzyme. About 1.0 kb BamHI fragments of PIP gene were fractionated on agarose gel and isolated by unidirectional electroelution.

Figure 3:
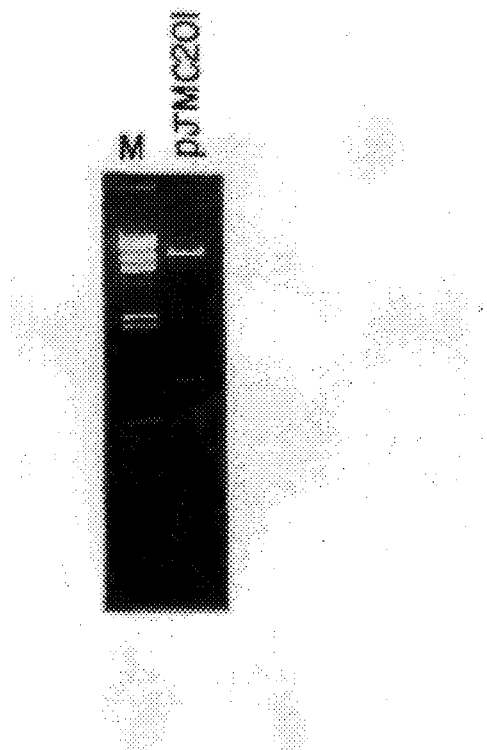
FIG. 3 is a photograph showing the agarose gel electrophoresis pattern of expression vector pJMC201 digested with restriction enzyme.

SstI restriction site near the Nos terminator of binary vector pBI121(Clonetech, Lot#6019-2, USA) was substituted with BamHI restriction site as follows: pBI121 was treated with SstI, and Klenow's fragment treatment and ligation with BamHI linker were carried out. Selection of DNA of interest followed. The selected DNAs were subject to BamHI digestion, then about 11.06 kb BamHI fragments of pBI121 were fractionated on agarose gel and isolated by unidirectional electroelution.

pJMC201 was prepared by ligating 11.06 kb BamHI fragment of pBI121 with 1.0 kb BamHI fragment of PIP gene by $T_4$ DNA ligase. pJMC201 thus obtained was introduced into competent XL1-BLUE treated with $CaCl_2$. Example 2 is schematically illustrated in FIG. 2. FIG. 3 shows agarose gel electrophoresis pattern of pJMC201 digested with BamHI. In FIG. 3, lane M is λDNA digested with HindIII as molecular marker and lane pJMC201 is vector pJMC201 digested with BamHI. As can be seen in FIG. 3, two bands of about 1.0 kb and about 11.06 kb fragments were observed.

EXAMPLE 3

Transformation of Potato by Agrobacterium Mediator

Freeze-thawing method was employed to transform *Agrobacterium tumefaciens* LBA 4404 with pJMC201 prepared in Example 2. To select *Agrobacterium tumefaciens* LBA 4404 transformed with pJMC201, plasmid DNA was isolated from the Agrobacterium by a quick-screening method (see: An, G. et al., Plant Molecular Biology Manual, Kluwer Academic Publishers, (1988)) and digested with BamHI. *Agrobacterium tumefaciens* LBA 4404 transformed with pJMC201 was deposited with the Korean Collection of Culture and Microorganism(KCCM), an international depository authority(IDA) on Jul. 18, 1994 as deposition No. KCCM-10056.

*Agrobacterium tumefaciens* LBA 4404 transformed with pJMC201(KCCM-10056), a mediator for plant cell transformation, was incubated in a shaking incubator at 28° C., 200 rpm for 18 hrs. After cell culture, said cells were harvested, emulsified with MS medium to the concentration of 1 to $2 \times 10^3$ cells/ml and employed for plant transformation.

Potato tubers were surface-sterilized with 70% ethanol for 1 min, then with 50% hyperchlorite for 2 min and washed with sterile distilled water for 3 times. The tubers were cut into pieces of 1 cm in length. The tuber pieces were co-cultivated with the Agrobacterium cells harboring the pJMC201 for 30 min and placed in MS medium containing 1.0 mg/l zeatin and 0.5 mg/l IAA(3-β-indoleacrylic acid) at 20° C. for 48 hrs under dark condition. The tuber pieces were induced to shoots by incubation on MS medium containing 1.0 mg/l zeatin, 0.5 mg/l IAA, 100mg/l kanamycin and 500 mg/l carbenicillin with 16 hrs light/8 hrs dark cycle under 3,000 lux. From the shoots was root generated on MS medium containing 250 mg/l carbenicillin and 100 mg/l kanamycin and regenerated potato plants were transferred to pot and adapted for later use.

Figure 4A:
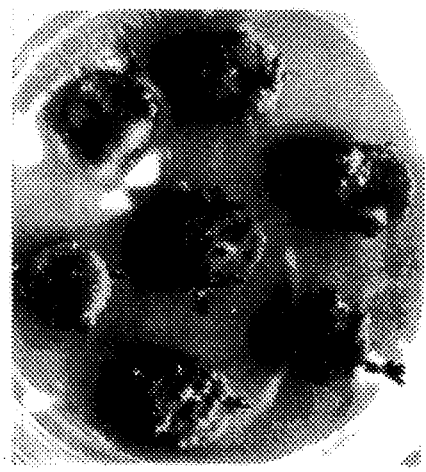
FIG. 4(A) is a photograph showing shoots induced from transgenic potato cell transformed with pJMC201.
Figure 4B:
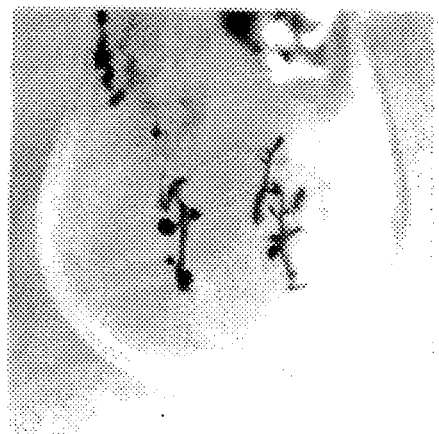
FIG. 4(B) is a photograph showing root generation from the shoots.

Shoots were induced on the MS medium 25 days after co-cultivation of the tuber pieces and the Agrobacterium cells harboring pJMC201 from the tuber pieces(see: FIG. 4(A)) and subject to root generation. Root was generated from most of regenerated shoots(see: FIG. 4(B)). Two of transgenic potato cell lines showed root generation were named with lines '2011'and '2012', respectively. Transgenic potato cell lines 2011 and 2012 grown up to 15 cm in length were employed for further experiments.

EXAMPLE 4

Identification of PIP Gene Insertion

Figure 5A:
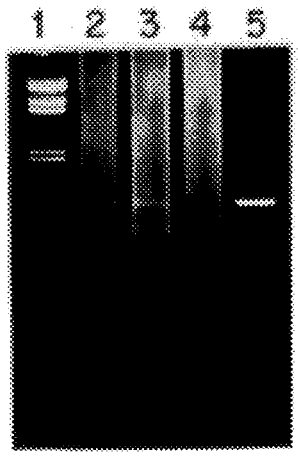
FIG. 5(A) is a photograph showing the agarose gel electrophoresis pattern of DNA isolated from transgenic potato plant of the invention.

Genomic DNA was purified from the transgenic potato and amplified by PCR employing primers used in Example 2. Each cycle of PCR needed denaturation(95° C., 1 min), annealing(60° C., 2 min) and extension(72° C., 2 min), and to effective amplification were 40 cycles required. The amplified DNAs were subject to electrophoresis on 0.8% agarose gel(see: FIG. 5(A)). In FIG. 5(A), lane 1 is λDNA digested with HindIII as molecular marker; lane 2 is DNA from line 2011; lane 3 is DNA from line 2012; lane 4 is DNA from nontransgenic potato; and, lane 5 is PIP gene isolated from cDNA library of *Phytolacca insularis Nakai*. As can be seen in FIG. 5(A), lanes 2, 3 and 5 showed bands of about 1.0 kb DNA fragment of PIP gene, while no band was showed in nontransgenic potato of lane 4. Accordingly, it was clearly demonstrated that PIP gene is properly inserted into the genome of transgenic potato.

Figure 5B:
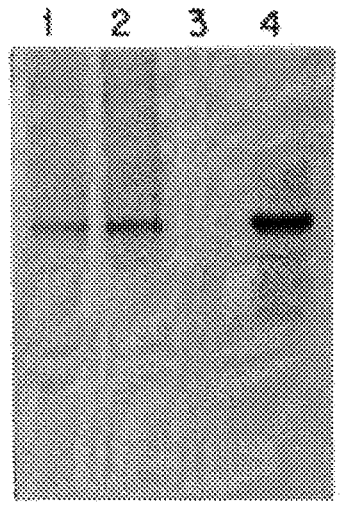
FIG. 5(B) is a photograph showing the Southern blot analysis result of total DNA isolated from transgenic potato plant of the invention.

To confirm whether said 1.0 kb DNA fragment is the PIP gene or not, the amplified DNAs were subject to Southern hybridization technique using the probe of 0.5 kb EcoRI fragment of the PAP cDNA labelled with the DIG-Labelling and Detection Kit used in Example 1 (see: FIG. 5(B)). In FIG. 5(B), lane 1 is DNA from line 2011; lane 2 is DNA from line 2012; lane 3 is DNA from nontransgenic potato; and, lane 4 is PIP gene isolated from cDNA library of *Phytolacca insularis Nakai*. As can be seen in FIG. 5(B), lanes 1, 2 and 4 showed bands of PIP gene hybridized with the probe, while no band was identified in nontransgenic potato of lane 3. Accordingly, it was clearly demonstrated that PIP gene is properly inserted into the genome of transgenic potato.

EXAMPLE 5

Determination of PIP Gene Transcription

Figure 6:
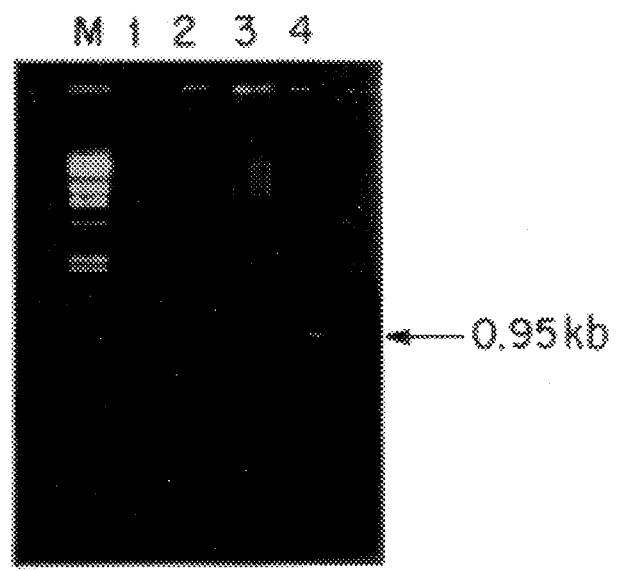
FIG. 6 is a photograph showing the Southern blot analysis result of cDNA isolated from transgenic potato plant of the invention.

Total cellular mRNA was isolated from transgenic potato and cDNA synthesized therefrom was amplified by PCR employing primers used in Example 2. Each cycle of PCR needed denaturation (95° C., 1 min), annealing(60° C., 1 min) and extension (60° C., 1 min), and to effective amplification were 35 cycles required. Amplified cDNAs were subject to electrophoresis on 0.8% agarose gel(see: FIG. 6). In FIG. 6, lane M is λDNA digested with HindIII as molecular marker; lane 1 is cDNA from line 2011; lane 2 is cDNA from line 2012; lane 3 is cDNA from non-transgenic potato; and, lane 4 is PIP gene isolated from cDNA library of *Phytolacca insularis Nakai*. As can be seen in FIG. 6, lanes 1, 2 and 4 showed about 1.0 kb DNA fragment of PIP gene, while no band was showed in nontransgenic potato of lane 3. Accordingly, it was concluded that PIP gene inserted into the genome of transgenic potato is transcribed in a proper manner.

EXAMPLE 6

Determination of Viral Resistance of Transgenic Potato

Transgenic potato lines 2011 and 2012 and nontransgenic potato were inoculated with PVX(potato virus X), PVY (potato virus Y) and PLRV(potato leafroll virus), respectively. PVX and PVY were inoculated on leaves after wounding with cotton wool treated with carborundum. PLRV was inoculated by mediation of 10 aphids(Myzus persicae) feeded for 3 days on potato leaves infected with PLRV, after which aphids were killed with insecticide.

The inoculated leaves were removed at 15, 30 and 45 days after inoculation and subject to ELISA assay to determine population of each virus(see: Clark, M. F. et al., J. Gen. Virol., 34:475–483(1977)). Microtiter plates with 98 wells were coated with 200 μl(per each well) of 1000-fold diluted polyclonal antibodies(BIOREBA AG Co., Germany) against each virus at 37° C. for 4 hrs. The plates were washed with PBS containing 0.05% Tween 20 for 3 times, reacted with 20 μl of leaf extract in phosphate buffered saline(PBS)(1:20= leaf extract:PBS, v/v) at 6° C. for 16 hrs and then with 200 μl of 1000-fold diluted polyclonal alkaline phosphatase-conjugated IgG(BIOREBA AG Co., Germany). After washing with PBS for 3 times, phosphatase activity was determined with 200 μl of p-nitrophenyl-phosphate(1 mg/ml) to produce p-nitrophenol whose absorbance is measured at 405 nm.

Figure 7:
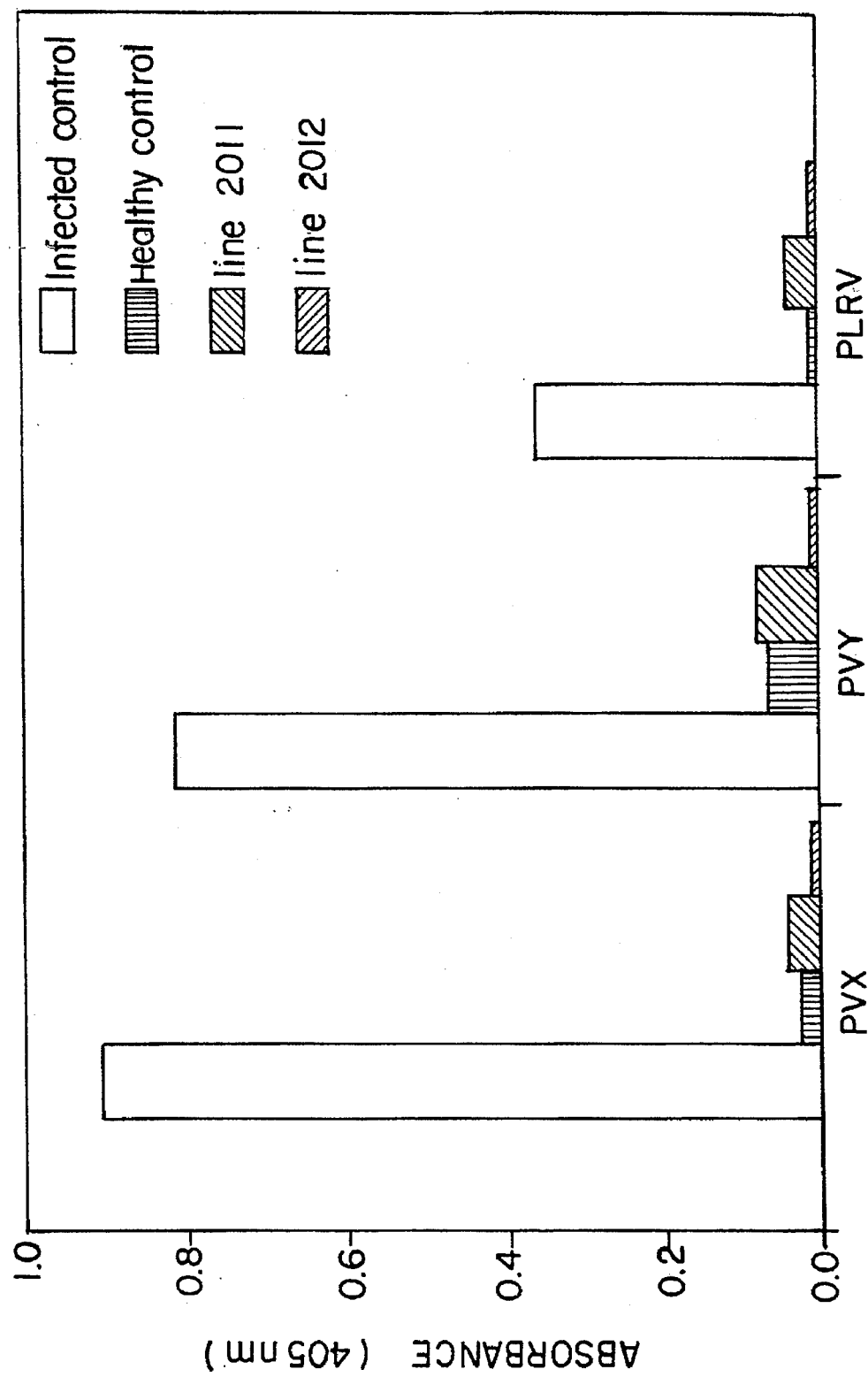
FIG. 7 is a graph showing broad spectrum of viral resistance in the transgenic potato plant of the invention.

FIG. 7 is a graph showing the results of ELISA at 45 days after inoculation. As can be seen in FIG. 7, transgenic plant lines 2011 and 2012 revealed lower levels of PVX and PVY than infected control plants, and the lines 2012, in particular, showed lower level than even healthy control plants (non-infected); and, the level of PLRV particles was also lower in transgenic plants than infected plants.

Figure 8A:
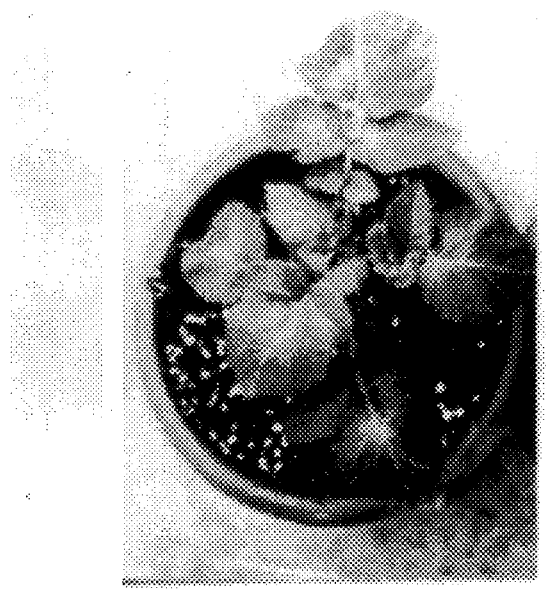
FIG. 8(A) is a photograph showing viral resistance for PVY(potato virus Y) in transgenic potato plant of the invention; and, FIG. 8(B) is a photograph showing no viral resistance for PVY in a nontransgenic potato plant.
Figure 8B:
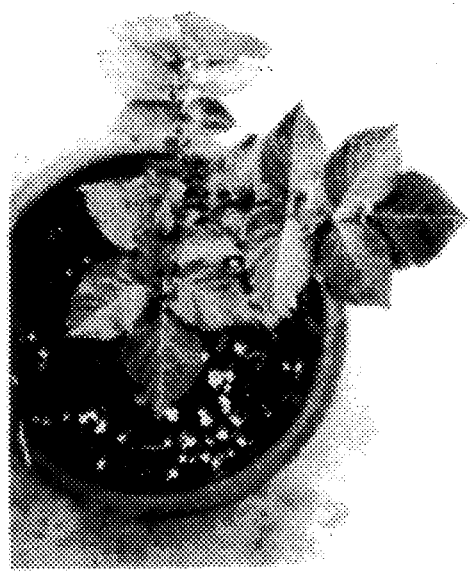

On the other hand, transgenic and nontransgenic potato plants were infected with PVY, respectively; and, symptom development on infected plants was examined with the naked eye. FIG. 8(A) shows viral resistance in transgenic potato plant of the invention, while FIG. 8(B) shows symptom of necrosis throughout veins in nontransgenic potato plant. Accordingly, it could be concluded that the transgenic plants produced by the invention are resistant to viral infection.

As clearly illustrated and demonstrated above, the present invention provides a process for preparing a transgenic plant producing antiviral protein, which is transformed with a recombinant vector for *Phytolacca insularis* antiviral protein expression. The transgenic potato plant of the invention was properly transformed with the recombinant vector; PIP was expressed from the transgenic plant in a successful manner; and, virus proliferation was efficiently inhibited by the expressed recombinant PIP in the transgenic potato.

What is claimed is:

1. A recombinant DNA pJMC201 which is capable of expressing *Phytolacca insularis* antiviral protein.

2. *Agrobacterium tumefaciens* LBA 4404 transformed with the recombinant DNA pJMC201 of claim 1(KCCM-10056).

3. A process for preparing *Phytolacca insularis* antiviral protein which comprises the step of culturing potato cells transformed with the recombinant DNA pJMC201 of claim 1.

4. A process for preparing virus-resistant transgenic plant which comprises the step of transforming a plant with the recombinant DNA pJMC201 of claim 1.

* * * * *

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 918 base pairs
        ( B ) TYPE: nucleic acid
        ( C ) STRANDEDNESS: single
        ( D ) TOPOLOGY: linear ( i i ) MOLECULE TYPE: cDNA to mRNA ( i i i ) HYPOTHETICAL: NO ( i v ) ANTI-SENSE: NO ( v i ) ORIGINAL SOURCE:
        ( A ) ORGANISM: Phytolacca insularis Nakai
        ( F ) TISSUE TYPE: leaf ( v i i ) IMMEDIATE SOURCE:
        ( B ) CLONE: PIP ( x i ) SEQUENCE DESCRIPTION: SEQ ID NO:1:

```
ATGAAGTTGA  TGCTTGTGGT  GACAATATCA  GTATGGCTCA  TTCTTGCACC  AACATCTACT    60
TGGGCCGTGA  ATACCATCAT  CTACCATGTT  GGAAGTACCA  CCATTAGAAA  CTATGCAACT   120
TTTGGATACT  TCGTACTGAA  GGCGAAGATC  CAAGTTATGT  GCTATGGAAT  ACCAATGCTG   180
CCCAATATTG  GATCAAATCC  AAAATACATA  TTGGTTGAGC  TCCAAGGTTC  AAATGAAGAA   240
GGCATCACAC  TAATGCTAAG  ACGAAACAAT  TTATATGTGA  TGGGCTATTC  TGATCCCTAC   300
AACAATAGGT  GTCGTTTCCA  TCTCTTTAAG  GCTATCTCAG  GTACTGAACG  CGAAGATGTA   360
GAGACTACTC  TTTGCCCAAA  TGCCGATTCT  CGTGTTGGTA  AAAACATAAA  CTATGATAGT   420
CGATATCCAA  CATTGGAATC  AAAAGCAGGA  GTAAATTCAA  GAAGTCGAGT  CCAACTGGGA   480
ATTCGAATAC  TCGACAGTGG  CATTGGAAGG  ATTTCTGGAG  TGACGTCATT  CACTGAGAGA   540
ACCGAAGCTG  AATTCCTACT  GGTAGCCATA  CAAATGGTAT  CAGAGGCAGC  AAGATTCAAG   600
TACATAGAGG  ATCAAGTGAA  AACTAATTTT  AACAGACCAT  TCAACCCTAA  TCCCAAAGTA   660
CTTATATTGC  AGGAGACATG  GGGTAAGATT  TCTTCAGCAA  TTCATGGTGC  CAGGAATGGA   720
GTTTACCCA   ATCCTCTACA  GCTAGTGCAT  GCCAATGGTG  CAAATTGGAT  AGTGTTGAGA   780
GTGGATGAAA  TCAAGCCTGA  TGTGTCACTC  TTAAACTACG  TTATTGGGAG  CTGCCAGAGA   840
ACTTATAACC  AAAATGCCAT  GTTTCTCAA   CTTATAATGT  CTACTTATTA  TAATTACATG   900
```

GCTAATCTTG GTGATTAG                                                                                          918

( 2 ) INFORMATION FOR SEQ ID NO:2:

( i ) SEQUENCE CHARACTERISTICS:
        ( A ) LENGTH: 305 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( v ) FRAGMENT TYPE: N-terminal ( v i ) ORIGINAL SOURCE:
        ( A ) ORGANISM: Phytolacca insularis Nakai ( v i i ) IMMEDIATE SOURCE:
        ( B ) CLONE: PIP ( x i ) SEQUENCE DESCRIPTION: SEQ ID NO:2:

```
Met Lys Leu Met Leu Val Val Thr Ile Ser Val Trp Leu Ile Leu Ala
 1               5                  10                  15

Pro Thr Ser Thr Trp Ala Val Asn Thr Ile Ile Tyr His Val Gly Ser
            20                  25                  30

Thr Thr Ile Arg Asn Tyr Ala Thr Phe Gly Tyr Phe Val Leu Lys Ala
        35                  40                  45

Lys Ile Gln Val Met Cys Tyr Gly Ile Pro Met Leu Pro Asn Ile Gly
    50                  55                  60

Ser Asn Pro Lys Tyr Ile Leu Val Glu Leu Gln Gly Ser Asn Glu Glu
65                  70                  75                  80

Gly Ile Thr Leu Met Leu Arg Arg Asn Asn Leu Tyr Val Met Gly Tyr
                85                  90                  95

Ser Asp Pro Tyr Asn Asn Arg Cys Arg Phe His Leu Phe Lys Ala Ile
            100                 105                 110

Ser Gly Thr Glu Arg Glu Asp Val Glu Thr Thr Leu Cys Pro Asn Ala
        115                 120                 125

Asp Ser Arg Val Gly Lys Asn Ile Asn Tyr Asp Ser Arg Tyr Pro Thr
    130                 135                 140

Leu Glu Ser Lys Ala Gly Val Asn Ser Arg Ser Arg Val Gln Leu Gly
145                 150                 155                 160

Ile Arg Ile Leu Asp Ser Gly Ile Gly Arg Ile Ser Gly Val Thr Ser
                165                 170                 175

Phe Thr Glu Arg Thr Glu Ala Glu Phe Leu Leu Val Ala Ile Gln Met
            180                 185                 190

Val Ser Glu Ala Ala Arg Phe Lys Tyr Ile Glu Asp Gln Val Lys Thr
        195                 200                 205

Asn Phe Asn Arg Pro Phe Asn Pro Asn Pro Lys Val Leu Ile Leu Gln
    210                 215                 220

Glu Thr Trp Gly Lys Ile Ser Ser Ala Ile His Gly Ala Arg Asn Gly
225                 230                 235                 240

Val Leu Pro Asn Pro Leu Gln Leu Val His Ala Asn Gly Ala Asn Trp
                245                 250                 255

Ile Val Leu Arg Val Asp Glu Ile Lys Pro Asp Val Ser Leu Leu Asn
            260                 265                 270

Tyr Val Ile Gly Ser Cys Gln Arg Thr Tyr Asn Gln Asn Ala Met Phe
        275                 280                 285

Ser Gln Leu Ile Met Ser Thr Tyr Tyr Asn Tyr Met Ala Asn Leu Gly
```

|     | 290 | 295 | 300 |
| --- | --- | --- | --- |
|     | Asp |     |     |
|     | 305 |     |     |

( 2 ) INFORMATION FOR SEQ ID NO:3:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: cDNA to mRNA ( i i i ) HYPOTHETICAL: NO ( v i ) ORIGINAL SOURCE:
        ( A ) ORGANISM: Phytolacca insularis Nakai ( v i i ) IMMEDIATE SOURCE:
        ( B ) CLONE: N-terminal primer ( x i ) SEQUENCE DESCRIPTION: SEQ ID NO:3:

CGGGATCCAG CTAGTAGGAA GGGAAGATG      29

( 2 ) INFORMATION FOR SEQ ID NO:4:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: cDNA to mRNA ( v i ) ORIGINAL SOURCE:
        ( A ) ORGANISM: Phytolacca insularis Nakai ( v i i ) IMMEDIATE SOURCE:
        ( B ) CLONE: C-terminal primer ( x i ) SEQUENCE DESCRIPTION: SEQ ID NO:4:

CGGGATCCAA ACTAATCACC AAGATTAGC      29